United States Patent

Baudry et al.

[11] Patent Number: 5,837,400
[45] Date of Patent: Nov. 17, 1998

[54] IONICALLY CONDUCTIVE MATERIALS INCLUDING BIS(PHENYLSULPHONYL) IMIDES

[75] Inventors: Paul Baudry, Avon; Hervé Majestre, Quimper; Léonard Reibel, Hoenheim; Sami Bayoud, Strasbourg, all of France

[73] Assignee: Electricite de France-Service National, Paris, France

[21] Appl. No.: 764,031

[22] Filed: Dec. 12, 1996

[30] Foreign Application Priority Data

Dec. 14, 1995 [FR] France .................... 95 14 870

[51] Int. Cl.⁶ .......................... H01M 6/18; H01M 10/40; H01M 6/16
[52] U.S. Cl. .......................... 429/192; 429/194; 429/197; 252/62.2
[58] Field of Search .................. 429/197, 194, 429/192; 252/62.2

[56] References Cited

U.S. PATENT DOCUMENTS

| | | |
|---|---|---|
| 2,292,998 | 8/1942 | Hentrich . |
| 3,546,180 | 12/1970 | Caldwell . |
| 4,097,282 | 6/1978 | Noonan et al. . |

FOREIGN PATENT DOCUMENTS

| | | |
|---|---|---|
| 96629 | 12/1983 | European Pat. Off. . |
| 898394 | 4/1945 | France . |
| 951473 | 10/1949 | France . |
| 2160550 | 6/1973 | France . |
| 2606217 | 6/1988 | France . |
| 946480 | 8/1956 | Germany . |
| 1004010 | 3/1957 | Germany . |
| 49333 | 8/1966 | Germany . |
| 2000927 | 7/1971 | Germany . |

OTHER PUBLICATIONS

Z. Kristallogr., vol. 210, No. 9, Sep. 1995, pp. 721–722, XP000196199 P. Bombicz et al.
Res. Discl., No. 205, May 1981, pp. 198–199, XP000578009.
Chemical Abstracts, vol. 85, No. 21, Nov. 22, 1976, USA, Ab. No. 159583.

*Primary Examiner*—John S. Maples
*Attorney, Agent, or Firm*—Sughrue, Mion, Zinn, Macpeak & Seas, PLLC

[57] ABSTRACT

The invention relates to ionically conductive materials including at least one compound corresponding to the following formula (I):

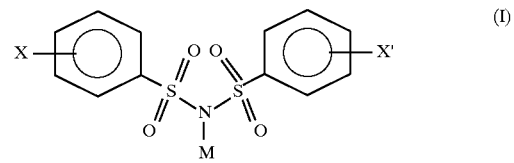

in which the groups X and X' are identical or different and denote at least one electrophilic group in an ortho, meta and/or para position and M denotes an alkali or alkaline-earth metal, in solution in a solvent including a macromolecular material or a polar aprotic solvent or solvent mixture. The electrophilic groups X, X' may be chosen from nitro, $C_1$–$C_5$ perfluoroalkyl, CN, halogen, vinyl, $CO_2R$ and $SO_2R$ groups where R denotes a $C_1$–$C_5$ linear or branched alkyl radical and the metal M may be chosen from lithium, sodium, potassium, caesium, magnesium, calcium and barium. The invention also relates to a process for the preparation of the abovementioned compounds. The invention applies more particularly to the manufacture of electrochemical generators including an electrolyte based, at least partially, on these ionically conductive materials.

26 Claims, 3 Drawing Sheets

IONICALLY CONDUCTIVE MATERIALS INCLUDING BIS(PHENYLSULPHONYL) IMIDES

The present invention lies in the field of ionically conductive materials intended to be employed especially as electrolytes in electrochemical current generators.

It relates more particularly to new salts called bis (phenylsulphonyl)imides, which can be used for the preparation of such electrolytes.

The invention relates to a process for the preparation of these salts.

It further relates to the ionically conductive materials obtained from these salts and the electrochemical generators containing them.

Ionic salts capable of resulting in the formation of solid solutions, capable of being employed in the production of electrochemical current generators, are known.

Document EP-A-0 096 629 described especially alkali metal perhalosulphonylimides in which the perhaloalkyl chain contains from 1 to 4 carbon atoms, the halogen being preferably fluorine and the alkali metal being preferably lithium or sodium.

It also describes the preparation of solid electrolytes from these salts, by dissolving in a macromolecular material such as poly(propylene oxide) and poly(ethylene oxide).

The solid electrolytes thus obtained can be used for the production of both primary and secondary electrochemical generators.

Another class of electrolytes which are in the liquid state is also known, for the production of such generators.

Thus, document FR-A-2 606 217 described an ionically conductive material including a salt in solution in a polar aprotic liquid solvent, the salt corresponding to the one of the following formulae:

$$M[RF-SO_2-N-SO_2-R'F] \quad (I)$$

$$M[RF-SO_2-N-CO-R'F] \quad (II)$$

$$M[RF-CO-N-CO-R'F] \quad (III)$$

$$M[QF\underset{SO_2}{\overset{SO_2}{\diagdown\hspace{-0.3em}\diagup}}N] \quad (IV)$$

in which M is an alkali or alkaline-earth metal, a transition metal or a rare earth; RF and R'F are identical or different and each denotes a perhalo, preferably perfluoro, radical containing from 1 to 12 carbon atoms; QF is a divalent perfluoro radical containing from 2 to 6 carbon atoms.

Linear ethers, esters, nitriles, nitro derivatives, amides and sulphones can be used as solvent.

These electrolytes can be used for the production of rechargeable generators.

A secondary electrochemical storage battery with non-aqueous electrolyte has also recently been described in document EP-A-0 482 287, in which the nonaqueous electrolyte results from the dissolving of a salt in a solvent containing a cyclic ester and a linear ester. The salt is preferably chosen from lithium tetrafluoroborate, lithium hexafluorophosphate, lithium hexafluoroacetate, lithium trifluoromethanesulphonate and lithium perchlorate.

An objective of the present invention is to provide new compounds that can be used for the preparation of an ionically conductive material, in solid or liquid form, which are intended especially for the production of electrochemical current generators.

Another objective is to provide a new process for the preparation of symmetric or asymmetric imides.

A further objective of the present invention is to provide new ionically conductive materials which are useful especially as electrolytes in electrochemical generators.

To this end the subject-matter of the invention is the use of compound corresponding to the following formula (I):

$$X\text{-}\underset{}{\bigcirc}\text{-}\underset{\underset{O}{\overset{O}{\|}}}{\overset{}{S}}\text{-}\underset{\underset{M}{\overset{}{|}}}{\overset{}{N}}\text{-}\underset{\underset{O}{\overset{O}{\|}}}{\overset{}{S}}\text{-}\underset{}{\bigcirc}\text{-}X' \quad (I)$$

in which groups X and X' are identical or different and denote at least one electrophilic group in an ortho, meta and/or para position and M denotes an alkali or alkaline-earth metal, for the preparation of ionically conductive material.

Another subject matter of the invention is a process for the preparation of the above compounds of formula (I), characterized in that it includes the stages consisting in:

a) preparing the sulphonamide of following formula (III):

$$(X,X')\text{-}\underset{}{\bigcirc}\text{-}\underset{\underset{O}{\overset{O}{\|}}}{\overset{}{S}}\text{-}NH_2 \quad (III)$$

in which (X, X') denotes at least one electrophilic group in an ortho, meta and/or para position, from the corresponding sulphonyl chloride of following formula (II):

$$(X,X')\text{-}\underset{}{\bigcirc}\text{-}\underset{\underset{O}{\overset{O}{\|}}}{\overset{}{S}}\text{-}Cl \quad (II, II')$$

in which (X, X') is as defined above, in the presence of aqueous ammonia;

b) preparing the alkali or alkaline-earth metal amide of following formula (IV):

$$(X,X')\text{-}\underset{}{\bigcirc}\text{-}\underset{\underset{O}{\overset{O}{\|}}}{\overset{}{S}}\text{-}NH\text{-}M \quad (IV)$$

in which (X, X') and M have the same meanings as above, from the sulphonamide (III), with the aid of a base in aqueous medium;

c) reacting the amide of formula (IV) with the sulphonyl chloride of formula (II, II') in aqueous medium to form the desired imide (I).

A further subject-matter of the invention is an ionically conductive material including at least one compound of formula (I) in solution in a solid or liquid solvent.

Finally, a subject-matter of the invention is an electrochemical generator characterized in that it includes an electrolyte made up, at least partially, of an ionically conductive material such as the above-mentioned.

The compounds used according to the invention correspond to the formula (I) given above.

According to the invention the term "phenyl" denotes a phenyl radical at least monosubstitutd by an electrophilic group X or X'.

These electrophilic groups are advantageously chosen from nitro, $C_1$–$C_5$ perfluoroalkyl, CN, halogen (preferably F or Br), vinyl, $CO_2R$ and $SO_2R$ groups, where R denotes a $C_1-C_5$ linear or branched alkyl radical. Nitro and trifluoromethyl groups are preferred.

The electrophilic group(s) X or X' may be situated in an ortho, meta and/or para position.

The phenyl radical may be monosubstituted in an ortho, meta or para position, the para position being preferred.

According to the invention M denotes a metal chosen especially from the group including Li, Na, X, Cs, Mg, Ca and Ba. It previously denotes lithium or sodium, lithium being the most preferred metal.

Insofar as obtaining symmetric imides is concerned, in the literature (G. Dauphin and A. Kergomard, Bull. Soc. Chim. Fr., 3, 486 (1961); U.S. Pat. No. 2,348,226) there are examples of preparation by direct coupling of two equivalents of the corresponding sulphonyl chloride in the presence of $NH_4OH$ and in aqueous medium, the pH being maintained at 10–11 by addition of NaOH.

Nevertheless, when it is desired to prepare lithium, and no longer sodium, imides by replacing sodium hydroxide with lithium hydroxide, this method produces mixtures of products and is therefore not satisfactory.

The inventors have found a new method for the preparation of imides, enabling the desired product to be obtained in good yields.

They have shown that it is possible to obtain the imide by coupling the corresponding amide (IV), prepared from the sulphonyl chloride (II), with the starting sulphonyl chloride (II) in the case of symmetric imides, or with another, appropriately substituted, sulphonyl chloride (II') in the case of asymmetric imides (X different from X').

More precisely, the starting material employed is a sulphonyl chloride of following formula (II):

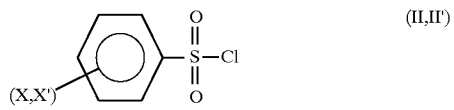

carrying a phenyl group suitably substituted by at least one electrophilic group (X, X') (that is to say a phenyl group corresponding to the substituted phenyl group of the desired final product), which is treated with excess aqueous ammonia, which produces the corresponding sulphonamide of the following formula (III):

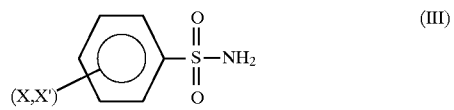

The sulphonamide (III) is isolated by filtration after precipitation by acidifying the mixture.

This sulphonamide (III) is next converted to the corresponding amide of the following formula (IV):

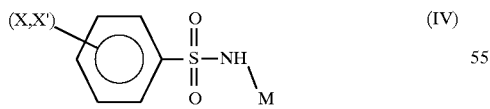

by treatment with the aid of a basic aqueous solution, for example a solution of LiOH or NaOH, depending on whether it is desired to obtain the lithium or sodium amide.

The desired imide (I) is finally obtained by coupling, in aqueous medium, of the amide (IV) obtained previously with sulphonyl chloride (II) also employed as starting material. The imide thus obtained is symmetric (X and X' are identical).

In accordance with the invention two equivalents of sulphonamide (IV) are advantageously employed, which is prepared beforehand and which is reacted directly with one equivalent of sulphonyl chloride (II) in water.

The inventors have found that it is more efficient to employ the amide (IV) both as nucleophile and as base, rather than to employ lithium hydroxide or sodium hydroxide as base.

In addition, in parallel with the imide (I), the sulphonamide (III) is also collected, which can thus be recycled in order to obtain the corresponding amide (IV).

According to the invention it is also possible to prepare asymmetric imides, that is to say compounds of formula (I) in which X and X' are different.

In this case the coupling of the amide (IV) carrying the desired substituent(s) X is carried out with sulphonyl chloride (II') carrying the desired substituent(s) X', or vice versa.

The compounds (I) according to the invention are particularly suited for the preparation of ionically conductive materials.

In fact, in accordance with the invention, such materials can be obtained by dissolving at least one compound (I) in a solid or liquid solvent.

The solid solvent may consist of a macromolecular material made up, at least partially, of a polymer in which the monomer units contain at least one heteroatom, especially oxygen or nitrogen, capable of forming bonds of donor-acceptor type with the compounds(s) of formula (I).

The ratio of the number of heteroatoms originating from the monomer units of the said polymer to the number of alkali metal atoms is advantageously between 4 and 100 and preferably between 8 and 30.

The macromolecular materials employed according to the invention may consist of homopolymers or copolymers.

These are preferably poly(ethylene oxide) or poly (propylene oxide).

The proportion of the compound(s) (I) is, of course, chosen so as to be smaller than the solubility threshold of this (these) compound(s) in the selected macromolecular material.

The preparation of the ionically conductive material is carried out by any known method.

It can thus be performed by dissolving in a solvent both for the polymer and the compound(s) (I), such as, for example, acetonitrile or methanol, and then removing this solvent.

It is also possible to proceed without any solvent, by dissolving the compound(s) (I) in the polymer in the molten state.

According to the invention it is also possible to prepare an ionically conductive material by dissolving at least one compound (I) in a liquid solvent.

This may be a polar aprotic solvent chosen from the group including:

linear ethers such as diethyl ether or dimethoxyethane or cyclic ethers such as tetrahydrofuran, dioxane or dimethyltetrahydrofuran, esters such as methyl or ethyl formate, propylene or ethylene carbonate or butyrolactones, nitriles such as acetonitrile and benzonitriles, nitro derivatives such as nitromethane or nitrobenzene, amides such as dimethylformamide, diethyleformamide and N-methylpyrrolidone, and sulphones such as dimethyl sulphone, tetramethyl sulphone, lactones and α-valerolactones and sulpholane.

A mixture of these solvents can also be employed.

As in the case of solid materials, the proportion of the compound(s) (I) must remain lower than the solubility threshold of this (these) compound(s) in the solvent or solvent mixture employed.

The ionically conductive materials thus obtained have a conductivity enabling them to be employed in particular as electrolytes for electrochemical current generators.

According to the invention solid or liquid electrolytes can thus be prepared for primary or secondary electrochemical generators which may also be of rechargeable type.

To produce an electrochemical generator, an electrolyte made up, at least partially, of an ionically conductive material as described above is used in combination with a negative electrode made of a material capable of supplying alkali metal ions corresponding to the alkali metal M of the chose compound (I) and with a positive electrode made of a material capable of incorporating the atoms of this metal.

It is possible, for example, to employ a negative electrode made up of an alloy, of an intermetallic compound or of an insertion compound based on this metal.

The positive electrode, for its part, may be made up of any material with a crystal structure permitting the insertion of alkali metals.

The presence of compounds (I) according to the invention in electrolytes for a generator and in particular of the rechargeable storage battery type makes it advantageously possible to delay the appearance of arborescences of dendritic type during the recharging of the storage battery and thus has the effect of improving the cyclability of the latter.

The concentration of compound(s) (I) is advantageously adjusted to obtain at the same time an ionic conductivity and an antidendrite effect which are both satisfactory.

According to the invention it is also possible to envisage an electrolyte including at least one compound (I) in combination with another salt exhibiting conductive properties, such as an alkali or alkaline-earth metal bis (perhaloalkylsulphonyl)imide, especially lithium bis (trifluoromethylsulphonyl)imide.

In the case of an electrolyte based on poly(ethylene oxide) PEO, for example, containing at least one compound (I) and another salt exhibiting conductive properties of the above-mentioned type, the concentration of compound(s) (I) in relation to the total concentration of the salts (imides) present in the PEO, is preferably between 1 and 70 mol %, still more preferably between 1 and 30 mol %.

BRIEF DESCRIPTION OF THE DRAWINGS

Other characteristics and advantages of the invention will emerge from the examples given below by way of illustration and without any limitation being implied, and from the appended drawings, in which.

EXAMPLES

Figure 1A:
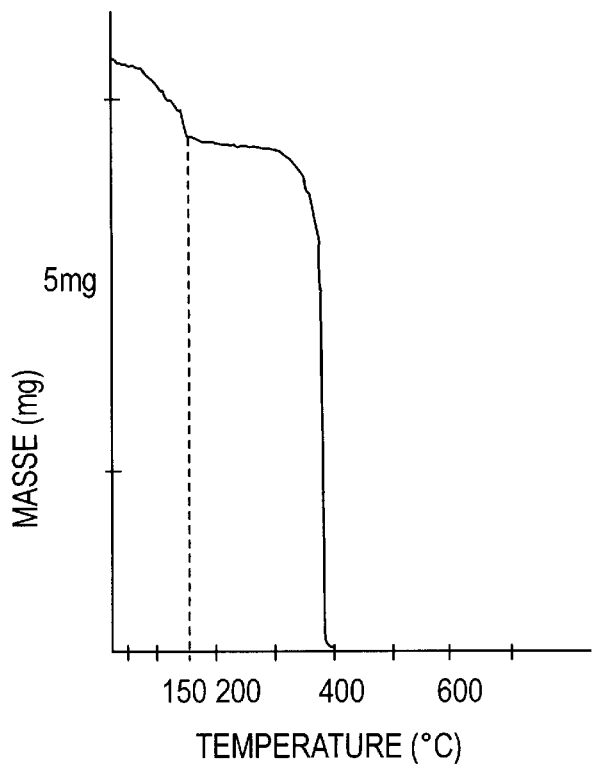
FIGS. 1A and 1B show the plots of thermogravimetric analysis between 35° C. and 798° C. in an inert and oxidizing atmosphere, in the case of an imide of formula (I) according to the invention, in which X=X' and denotes a nitro group in a para position and M denotes lithium.
Figure 1B:
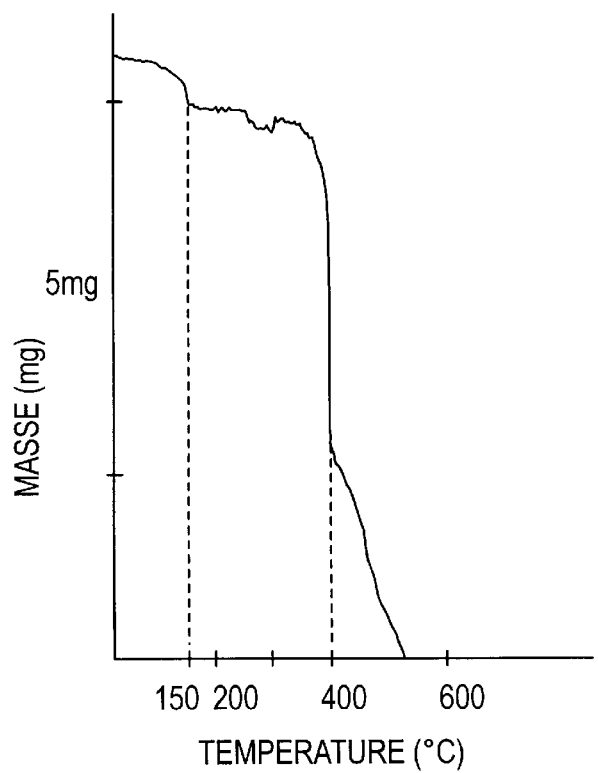

In all that follows, the symbol "X—Ph" or "X'—Ph" denotes a phenyl radical which has at least one electrophilic substituent X or X' and "p" denotes the para position.

The chemical shifts in the NMR spectra are expressed in ppm and the multiplicity (s=singlet, d=doublet), the number of hydrogens and the attributions (ArH=aromatic H) is shown in brackets.

Example 1

Preparation of Lithium bis(para-nitrophenylsulphonyl)imide

Stage a: Preparation of para-nitrophenylsulphonamide (III with X=p—NO$_2$)

The sulphonamide (III) in which the phenyl group is para-substituted by a nitro group (p—NO$_2$—Ph—SO$_2$NH$_2$) is prepared by treating the corresponding sulphonyl chloride (II) (p—NO$_2$—Ph—SO$_2$Cl) with an excess of aqueous ammonia solution according to the method described in the literature (G. Dauphin and A. Kergomard, Bull. Soc. Chim. Fr., 3, 486 (1961).

After reaction the mixture is acidified with hydrochloric acid and is filtered to recover the precipitated sulphonamide p—NO$_2$—Ph—SO$_2$NH$_2$.

The product obtained is purified by washing with water and with dichloromethane.

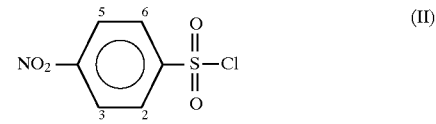

para-nitrophenylsulphonyl chloride (II):
$^1$H-NMR (DMSO-d$_6$): 8.21, 8.17, (d, 2H, ArH5 and H3); 7.84, 7.81 (d, 2H, ArH6 and H2).

para-nirophenylsulphonamide (III):
$^1$H-NMR (DMSO-d$_6$): 8.43, 8.38 (d, 2H, ArH5 and H3); 8.08, 8.03 (d, 2H, ArH6 and H2); 7.72 (s, 2H, NH$_2$).

Stage b: Preparation of lithium para-nitrophenylsulphonamide (IV with X=p—NO$_2$ and M=Li)

The sulphonamide (III) is treated with an aqueous solution containing one equivalent of lithium hydroxide. After reaction the product is isolated by evaporation of the solvent.

$^1$H-NMR (DMSO-d$_6$): 8.17, 8.14, (d, 2H, ArH5 and H3); 7.88, 7.84 (d, 2H, ArH6 and H2); 3.3 (broad peak, 1H, —NH—).

Stage c: Preparation of lithium bis(para-nitrophenylsulphonyl)imide (I with X=NO$_2$ and M=Li)

Two equivalents of sulphonamide (IV) obtained previously in stage b are reacted with one equivalent of the starting sulphonyl chloride (II) in the presence of water.

In parallel with the formation of the required imide (I), para-nitrosulphonamide (III) is also formed, which precipitates out of the aqueous solution and which is subsequently reusable. The imide (I) is isolated by evaporation of the solvent and then recrystallized after redissolving in hot water.

After recrystallization of the imide (I) obtained by concentration of the aqueous solution and redissolving with heating, it is vacuum-dried at 80° C. 24 hours, which yields the pure product in an 88% yield.

Elemental analysis of the product thus isolated confirms the absence of any other product.

$^1$H-NMR (DMSO-d$_6$, D$_2$O): 8.24, 8.21 (d, 4H, ArH3, H5, H3', H5') 7.91, 7.87 (d, 4H, ArH2, H6, H2', H6').

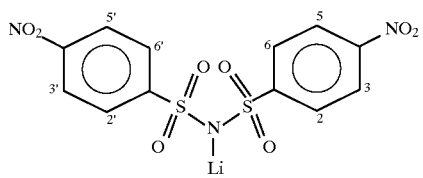

$^{13}$C-NMR (DMSO-d$_6$, D$_2$O): 151.6 (C4 and C4'); 1.45.4 (C1 and C1'); 126.4 (C2 and 2', C6 and C6'); 123.9 (C3 and C3', C5 and C5').

The attribution of the various lines has been carried out with the aid of the spectrum of the lithium arylsulphonamide and by employing the CHEMWIND software for predicting the shifts of the carbons in the imide.

Thermogravimetric analysis: This is carried out between 35° C. and 798° C. with a rate of temperature rise of 10°/minute in inert and oxidizing atmospheres.

The plots obtained are given in FIGS. 1A (in N$_2$) and 1B (in air).

These plots show the presence of water, which is eliminated at 150° C. This high value shows a high energy of salvation of the salt by water.

They also show that the salt (I) is stable up to 370° C. in an inert or oxidizing (ambient air) medium.

Example 2
Preparation of Lithium 4-nitro-4'-vinylbiphenylsulphonylimide

The procedure is as in Example 1 for the preparation of lithium para-styrenesulphonamide (IV with X'=p-vinyl and M=Li) from para-styrenesulphonamide chloride (II' with X'=p-vinyl).

para-styrenesulphonyl chloride:
$^1$H-NMR (DMSO-d$_6$): 7.58, 7.54 (D, 2H, ArH2' and H6'); 7.43, 7.39 (d, 2H, ArH3' and H5'); 6.79, 6.73, 6.70, 6.65 (dd, 1H, =CH—); 5.87, 5.78 (d, 1H, H2C=); 5.29, 5.24 (d, 1H, H2C=).

para-styrenesulphonamide;
$^1$H-NMR (DMSO-d$_6$): 7.58, 7.54 (d, 2H, ArH2' and H6'); 7.43, 7.39 (d, 2H, ArH3' and H5'); 6.79, 6.74, 6.70, 6.65 (dd, 1H, =CH—); 5.87, 5.78 (d, 1H, H2C=); 5.29, 5.23 (d, 1H, H2C=).

The coupling of the para-styrenesulphonamide (IV) thus prepared with para-nitrophenylsulphonyl chloride (II) is next preformed in the conditions described in stage c) of Example 1. The desired asymmetric imide, lithium 4-nitro-4'-vinylbiphenylsulphonylimide is thus obtained.

$^1$H-NMR (DMSO-d$_6$): 8.21, 8.17 (d, 2H, ArH5 and H3); 7.87, 7.83 (d, 2H, ArH6 and H2); 7.60, 7.56 (d, 2H, ArH2' and H6'); 7.46, 7.42 (d, 2H, ArH3' and H5'); 6.81, 6.75, 6.72, 6.66 (dd, 1H, =CH—); 5.92, 5.83 (d, 1H, H2C=); 5.36, 5.30 (d, 1H, H2C=).

$^{13}$C-NMR: 151.6 (C4); 145.4 (C1); 140.6 (C4'); 138.5 (C1'); 135.8 (vinyl CH); 126.5 (C3' and C5'); 126.4 (C2 and C6); 125.4 (C2' and C6'); 123.9 (C3 and C5); 112.4 (vinyl CH$_2$).

The attribution of the various lines was carried out with the aid of the spectrum of lithium arylsulphonamide and by employing the Chemwind software for predicting the shifts of the carbons in the imide.

Elemental analysis: after vacuum-evaporation at 80° C. C=43.61%; H=3.11%; N=7.34%; Li=1.770%; H$_2$O=2.934%.

after treatment with acetonitrile and vacuum-evaporation at 50° C. C=43.99%; H=3.62%; N=6.58% Li=1.545%, H$_2$O=2.658%.

Study of Conductivity

The salt of obtained in Example 1, given above, was studied for its properties of conduction in a polymer electrolyte system.

Several samples of poly(ethylene oxide) PEO 900×10$^3$ containing lithium bis(para-nitrophenylsulphonyl)imide (NO$_2$PhSILi) with various salt contents represented by the O/Li ratio.

Figure 2:
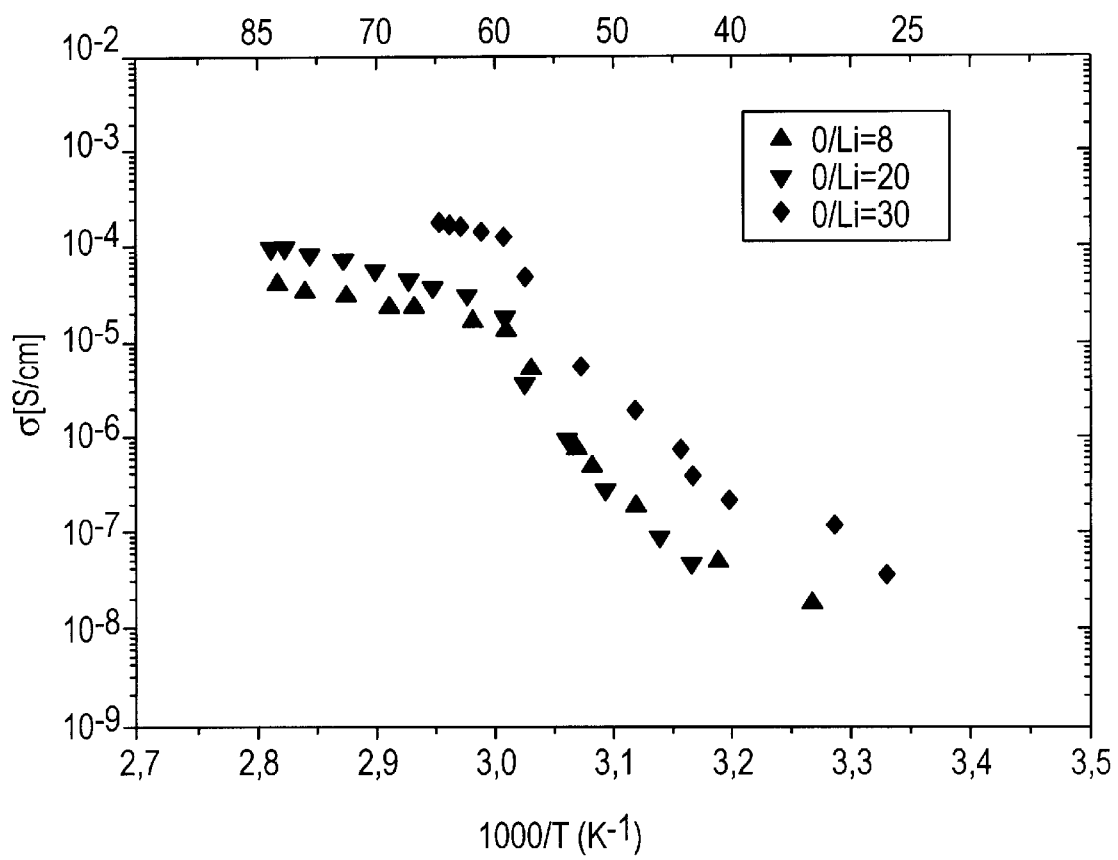
FIG. 2 shows the curves of conductivity as a function of the temperature for an ionically conductive material according to the invention including an imide of formula (I) in which X=X' and denotes a nitro group in a para position and M denotes lithium, in solution in poly(ethylene oxide), at various salt concentrations.

FIG. 2 gives the conductivity curves obtained as a function of 1/T, the measurements being performed at increasing temperatures.

It can be seen that the best results are obtained with an O/Li ratio=30.

The conductivities are low at ambient temperature (10$^{-8}$ S/cm) because of the crystallinity of the PEO, and then increase rapidly to reach the order of 10$^{-4}$ S/cm at 60° C. in the case of O/Li=30.

Example 3
Manufacture of a Rechargeable Storage Battery

A 7 cm$^2$ electrochemical cell is formed, consisting of two lithium electrodes separated by a polymer electrolyte based on poly(ethylene oxide) PEO and including a mixture of lithium bis(trifluoromethylsulphonyl)imide (LiTFSI) and of lithium bis(para-nitrophenylsulphonyl)imide (LiNPSI) in an LiNPSI/LiTFSI molar ratio of 0.5, such that the overall O/Li ratio (taking both the lithium salts present into account) is 30.

Study of the Antidendrite Effect

Starting with an electrochemical cell according to Example 3, the time at the end of which the cell is short-circuited under the effect of the dendritic growth is measured in the case of an applied constant current of 0.1 mA/cm$^2$.

Figure 3:
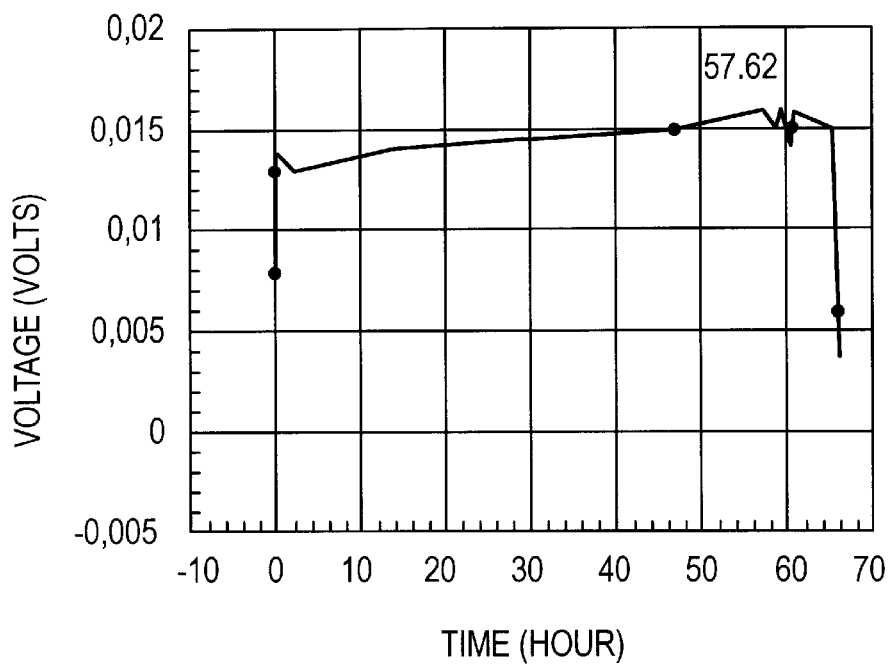
FIG. 3 shows a curve indicating the period at the end of which short-circuiting occurs in the case of a rechargeable storage battery provided with a polymer electrolyte including a compound (I) according to the invention.

FIG. 3 shows the results obtained.

By way of comparison an electrochemical cell of the same type as in Example 3 is produced, with the exception of the PEO-based electrolyte, which includes only lithium bis (trifluoromethylsulphonyl)imide (LiTFSI) according to an O/Li ratio=30.

Figure 4:
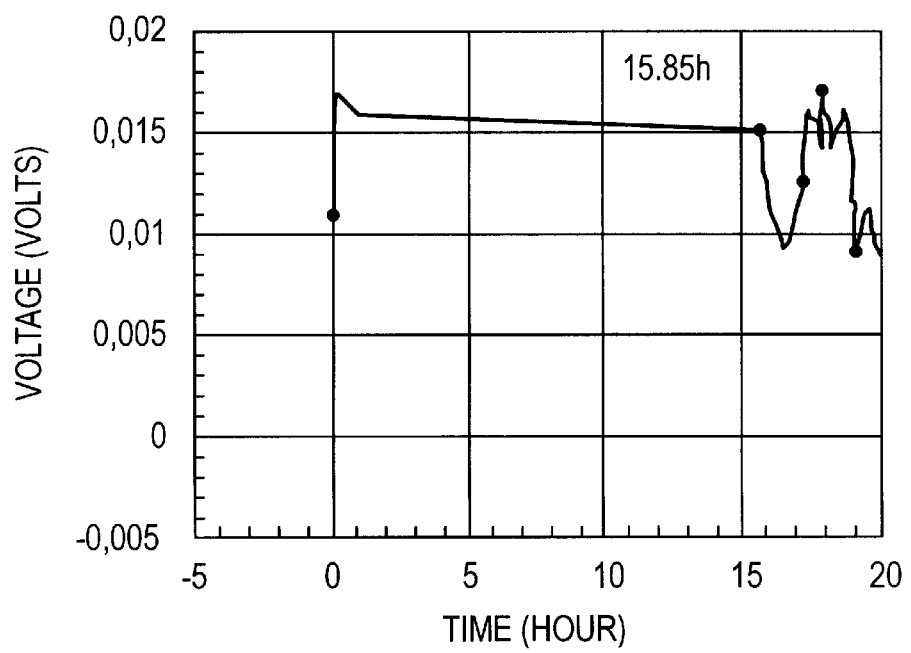
FIG. 4 shows a curve indicating the period at the end of which the short-circuiting occurs in the case of a rechargeable storage battery provided with a known polymer electrolyte.

FIG. 4 shows the results obtained for this comparative example.

It is seen that when the compound according to the invention is present (LiNPSI), the short circuit occurs only after approximately 60 hours, whereas in the case of the known electrolyte the short circuit occurs after only approximately 15 hours.

This shows that the presence of a compound according to the invention makes it possible to obtain a more homogeneous lithium deposit when compared with the case in which it is absent.

We claim:

1. Ionically conductive material comprising at least one compound of formula (I):

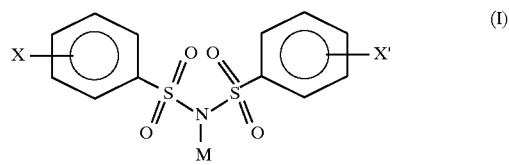

in which X and X' are identical or different and denote at least one electrophilic group in an ortho, meta and/or para position and M denotes an alkali or alkaline-earth metal, in solution in a solid solvent consisting of a macromolecular material made up, at least partially, of a polymer in which the monomer units contain at least one heteroatom, selected from the group consisting of oxygen and nitrogen, capable of forming donor-acceptor bonds with the at least one compound of formula (I).

2. Ionically conductive material according to claim 1, wherein the electrophilic groups X, X' are chosen from nitro, $C_1$–$C_5$ perfluoroalkyl, CN, halogen, vinyl, $CO_2R$ and $SO_2R$ groups, where R denotes a $C_1$–$C_5$ linear or branched alkyl radical.

3. Ionically conductive material according to claim 1, wherein the electrophilic groups are chosen from nitro and trifluoromethyl groups.

4. Ionically conductive material according to claim 1, wherein the metal M is chosen from the group including lithium, sodium, potassium, caesium, magnesium, calcium and barium.

5. Ionically conductive material according to claim 1, wherein the metal M is an alkali metal chosen from lithium or sodium.

6. Ionically conductive material according to claim 1, wherein the phenyl radical is monosubstituted in the para position.

7. Ionically conductive material according to claim 1, comprising at least one compound chosen from lithium bis(para-nitrophenylsulphonyl)imide an lithium (4-nitro-4'-vinyldiphenylsulphonyl)imide.

8. Ionically conductive material according to claim 1, wherein the ratio of the number of heteroatoms originating from the monomer units of the said macromolecular material to the number of alkali metal atoms of the compound (I) is between 4 and 100.

9. Ionically conductive material according to claim 1, wherein the macromolecular material includes a polymer chosen from poly(ethylene oxide) and poly(propylene oxide).

10. Ionically conductive material according to claims 1 or 9, additionally includes at least one alkali or alkaline-earth metal bis(perhaloalkylsulphonyl)imide exhibiting conductive properties.

11. Ionically conductive material according to claim 10, wherein the alkali or alkaline-earth metal bis (perhaloalkylsulphonyl)imide is lithium bis (trifluoromethylsulphonyl)imide.

12. Ionically conductive material according to claim 10, wherein the concentration of compound(s) (I) in relation to the total concentration of active salts in between 1 and 70 mol %.

13. Ionically conductive material according to claim 12, wherein the concentration of the at least one compound of formula (I) in relation to the total concentration of active salts is from 1 to 30 mol %.

14. Ionically conductive material according to claim 1 wherein the ratio of the number of heteroatoms originating from the monomer units of the said macromolecular material to the number of alkali metal atoms of the compounds (I) is between 8 and 30.

15. Ionically conductive material comprising at least one compound of formula (I):

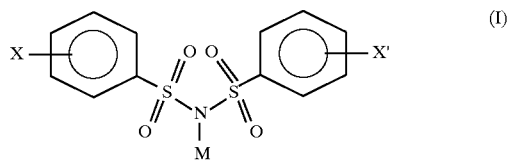

in which X and X' are identical or different and denote at least one electrophilic group in an ortho, meta and/or para position and M denotes an alkali or alkaline-earth metal, in solution in a liquid solvent made up of a polar aprotic solvent or solvent mixture selected from the group consisting of:
linear ethers selected from diethyl ether and dimethoxyethane and cyclic ethers selected from tetrahydrofuran, dioxane and dimethyltetrahydrofuran,
esters selected from methyl or ethyl formate, propylene or ethylene carbonate and butyrolactones,
nitriles selected from acetonitrile and benzonitriles,
nitro compounds selected from nitromethane and nitrobenzene,
amides selected from dimethylformamide, diethylformamide and N-methylpyrrolidone, and
sulphones selected from dimethyl sulphone, tetramethyl sulphone, lactones and α-valerolactones and sulpholane.

16. A process for preparing a ionically conductive material by placing a compound of following formula (I):

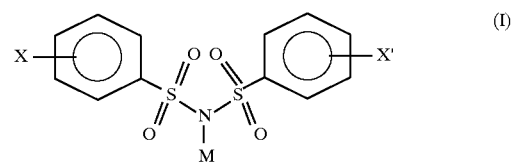

in which X and X' are identical or different and denote at least one electrophilic group in an ortho, meta and/or para position and M denotes an alkali or alkaline-earth metal,
a solid solvent consisting of a macromolecular material made up, at least partially, of a polymer in which the monomer units contain at least one heteroatom, selected from the group consisting of oxygen and nitrogen, capable of forming donor-acceptor bonds with the at least one compound of formula (I), or
a liquid solvent made up of a polar aprotic solvent or solvent mixture selected from the group consisting of:
linear ethers selected from diethyl ether and dimethoxyethane and cyclic ethers selected from tetrahydrofuran, dioxane and dimethyltetrahydrofuran,
esters selected from methyl or ethyl formate, propylene or ethylene carbonate and butyrolactones,
nitriles selected from acetonitrile and benzonitriles,
nitro compounds selected from nitromethane and nitrobenzene,
amides selected from dimethylformamide, diethylformamide and N-methylpyrrolidone, and
sulphones selected from dimethyl sulphone, tetramethyl sulphone, lactones and α-valerolactones and sulpholane.

17. A process according to claim 16, wherein the X and X' are selected from the group consisting of nitro, $C_1$–$C_5$ perfluoroalkyl, CN, halogen, vinyl, $CO_2R$ and $SO_2R$ groups where R denotes a $C_1$–$C_5$ linear or branched alkyl radical.

18. A process according to claim 16, wherein the X and X' are selected from the group consisting of nitro and trifluoromethyl groups.

19. A process according to claim 16, wherein M is selected from the group consisting of lithium, sodium, potassium, cesium, magnesium, calcium and barium.

20. A process according to claim 16, wherein M is alkali metal selected from the group consisting of lithium and sodium.

21. A process according to claim 16, wherein each phenyl radical is monosubstituted in the para position.

22. A process according to claim 16, wherein the at least one compound of formula (I) is selected from the group consisting of lithium bis(para-nitrophenylsulphonyl)imide and lithium (4-nitro-4'-vinyldiphenylsulphonyl)imide.

23. A process according to claim 16, wherein the at least one other active salt which is an alkali or alkaline-earth metal bis(perhaloalkylsulphonyl)imide exhibiting conductive properties is added.

24. A process according to claim 23, wherein the at least one other active salt is lithium bis(trifluoromethylsulfonyl) imide.

25. A process according to claims 23 or 24, wherein the concentration of the at least one compound of formula (I) in relation to the total concentration of active salts is between 1 and 70 mol %.

26. A process according to claim 25, wherein the concentration of the at least one compound of formula (I) in relation to the total concentration of active salts is between 1 to 30 mol %.

* * * * *